(12) United States Patent
Shome et al.

(10) Patent No.: US 9,126,045 B2
(45) Date of Patent: Sep. 8, 2015

(54) METHOD AND APPARATUS FOR ADAPTIVE CONTROL OF NEUROSTIMULATION USING CARDIAC RESTITUTION

(75) Inventors: Shibaji Shome, Arden Hills, MN (US);
Stephen Ruble, Lino Lakes, MN (US);
Jason J. Hamann, Blaine, MN (US);
Stephen J. Hahn, Shoreview, MN (US);
Arjun D. Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/586,503

(22) Filed: Aug. 15, 2012

(65) Prior Publication Data

US 2013/0053914 A1      Feb. 28, 2013

Related U.S. Application Data

(60) Provisional application No. 61/526,900, filed on Aug. 24, 2011.

(51) Int. Cl.
*A61N 1/365* (2006.01)
*A61N 1/36* (2006.01)

(52) U.S. Cl.
CPC ........ *A61N 1/36114* (2013.01); *A61N 1/36139* (2013.01)

(58) Field of Classification Search
CPC ............ A61N 1/3627; A61N 1/36114; A61N 1/3621; A61N 1/365; A61N 1/36014; A61N 1/362; A61N 1/3622; A61N 1/3625; A61N 1/36585; A61N 1/36592; A61N 1/3706; A61N 1/3956; A61B 5/0464; A61B 5/0402

USPC ....................... 600/515–518; 607/5–9, 17, 28
See application file for complete search history.

(56) References Cited

U.S. PATENT DOCUMENTS

| 5,330,507 | A  | 7/1994 | Schwartz |
| 5,555,889 | A  | 9/1996 | Karagueuzian et al. |
| 6,094,593 | A  | 7/2000 | Karagueuzian et al. |
| 6,920,353 | B1 | 7/2005 | Heinze et al. |

(Continued)

FOREIGN PATENT DOCUMENTS

| NO | WO-2013028431 A1 | 2/2013 |
| WO | WO-2005016450     | 2/2005 |
| WO | WO-2005035056 A1 | 4/2005 |

OTHER PUBLICATIONS

"international Application Serial No. PCT/US2012/050946, Search Report mailed Nov. 9, 2012", 4 pgs.

(Continued)

*Primary Examiner* — Rex R Holmes
(74) *Attorney, Agent, or Firm* — Schwegman Lundberg & Woessner, P.A.

(57) ABSTRACT

A neurostimulation system measures a cardiac parameter at various cardiac intervals and analyzes its restitution, including computing a restitution slope being a rate of change of the restitution parameter with respect to change in the cardiac interval. In various embodiments, the system uses the restitution slope to provide for adaptive control of neurostimulation. In various embodiments, one or more cardiac parameters such as action potential duration (APD), conduction velocity (CV), QT interval (QT), and/or T-wave morphology (TM) parameter are measured and analyzed for restitution of each parameter, which is then used to control the delivery of the neurostimulation.

25 Claims, 17 Drawing Sheets

(56) References Cited

U.S. PATENT DOCUMENTS

| | | | |
|---|---|---|---|
| 7,047,067 B2* | 5/2006 | Gray et al. | 600/516 |
| 7,415,307 B2* | 8/2008 | Sharma et al. | 607/17 |
| 7,801,601 B2 | 9/2010 | Maschino et al. | |
| 2005/0038478 A1 | 2/2005 | Klepfer et al. | |
| 2009/0299424 A1* | 12/2009 | Narayan | 607/9 |
| 2010/0233088 A1* | 9/2010 | Gilmour et al. | 424/9.2 |

OTHER PUBLICATIONS

"International Application Serial No. PCT/US2012/050946, Written Opinion mailed Nov. 9, 2012", 7 pgs.

"International Application Serial No. PCT/US2012/050946, International Preliminary Report on Patentability mailed Mar. 6, 2014", 9 pgs.

Li, Shao-Ru, et al., "Effect of vagus nerve on the action potential duration of ventricular cell of dog I. Effect of stimulation of vagus nerve and atropine", Journal of Huazhong University of Science and Technology—Medical Sciences, 5(3), (1985), 139-146.

Shome, S., et al., "Ischemic preconditioning protects against arrhythmogenesis through maintenance of both active as well as passive electrical properties in ischemic caine hearts", J Electrocardiol., 40(6 Suppl), (Nov.-Dec. 2007), S150-9.

Vigmond, E. J. at al., "The effect of vagally induced dispersion of action potential duration on atrial arrhythmogenesis", Heart Rhythm, 1(3), (Sep. 2004), 334-44.

\* cited by examiner

METHOD AND APPARATUS FOR ADAPTIVE CONTROL OF NEUROSTIMULATION USING CARDIAC RESTITUTION

CLAIM OF PRIORITY

This application claims the benefit of priority under 35 U.S.C. §119(e) of Shome et al., U.S. Provisional Patent Application Ser. No. 61/526,900, entitled "METHOD AND APPARATUS FOR ADAPTIVE CONTROL OF NEUROSTIMULATION USING CARDIAC RESTITUTION", filed on Aug. 24, 2011, which is herein incorporated by reference in its entirety.

TECHNICAL FIELD

This document relates generally to neurostimulation and more particularly to a system and method for controlling delivery of neurostimulation using cardiac restitution.

BACKGROUND

Neurostimulation has been applied to modulate various physiologic functions and treat various diseases. One example is the modulation of cardiac functions using autonomic modulation therapy (AMT) such as vagus nerve stimulation (VNS) therapy in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of VNS is utilized, for example, to control myocardial remodeling.

Because a patient's physiological conditions and response to AMT changes over time, there is a need for providing adaptive control of the therapy.

SUMMARY

A neurostimulation system measures a cardiac parameter at various cardiac intervals and analyzes its restitution, including computing a restitution slope being a rate of change of the cardiac parameter with respect to change in the cardiac interval. In various embodiments, the system uses the restitution slope to provide for adaptive control of neurostimulation. In various embodiments, one or more cardiac parameters such as action potential duration (APD), conduction velocity (CV), QT interval (QT), and/or T-wave morphology (TM) parameter are measured and analyzed for restitution of each parameter, which is then used to control the delivery of the neurostimulation.

In one embodiment, a neurostimulation system includes a stimulation output circuit, a sensing input, and a control circuit. The stimulation output circuit delivers neurostimulation. The sensing input receives one or more cardiac signals. The control circuit includes a measurement circuit, a restitution analyzer, and a stimulation controller. The measurement circuit measures a cardiac interval and a restitution parameter using the one or more cardiac signals. The restitution analyzer analyzes restitution of the restitution parameter and includes a slope computer. The slope computer computes a restitution slope using the values of the restitution parameter measured at a plurality of cardiac intervals. The restitution slope is a rate of change of the restitution parameter with respect to change in the cardiac interval. The stimulation controller controls the delivery of the neurostimulation using the restitution slope.

In one embodiment, a method for controlling delivery of neurostimulation is provided. One or more cardiac signals are sensed. A restitution parameter is measured using the sensed one or more cardiac signals at a plurality of cardiac intervals covering a specified range of cardiac intervals. A restitution slope is computed using the values of the restitution parameter measured at the plurality of cardiac intervals. The restitution slope is the rate of change of the restitution parameter with respect to change in the cardiac interval. The delivery of the neurostimulation is controlled using the restitution slope.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
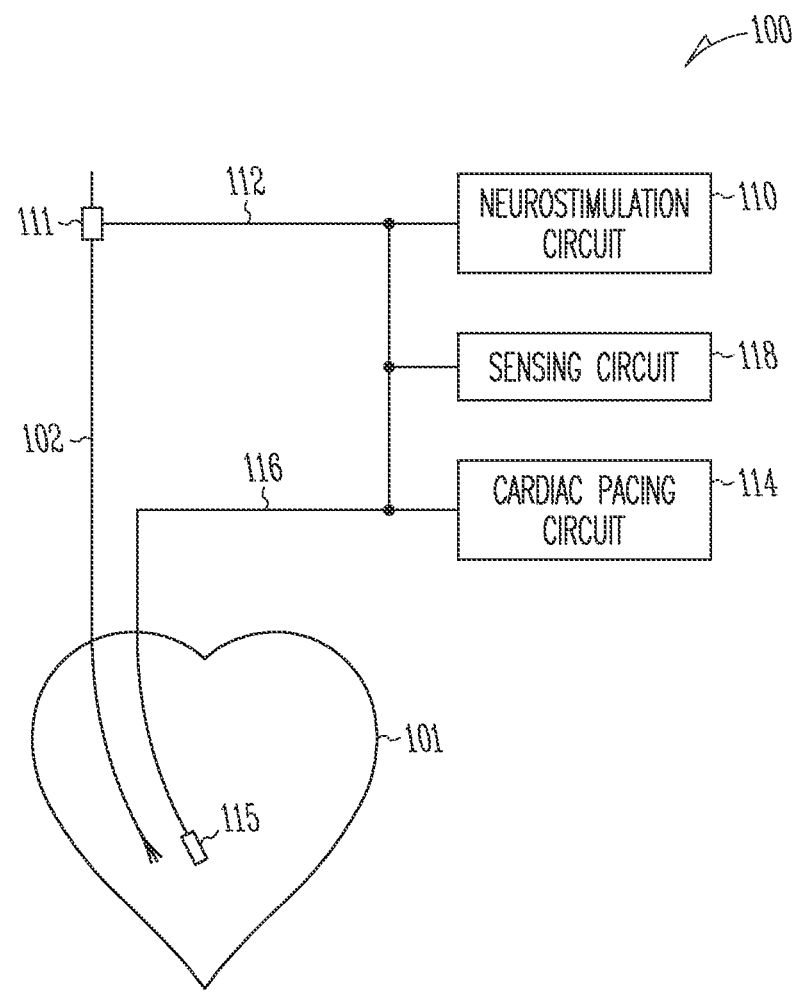
FIG. 1 is an illustration of an embodiment of a neurostimulation system and portions of an environment in which the neurostimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for adaptive control of neurostimulation therapy using one or more sensed parameters indicative of cardiac restitution. The neurostimulation includes autonomic modulation therapy (AMT). Cardiac restitution indicates dynamic electrophysiological heterogeneity of cardiac tissue. In various embodiments, the adaptive control includes therapy titration for maintaining effectiveness of the neurostimulation in modulating one or more cardiovascular functions.

In various embodiments, restitution of one or more cardiac parameters is analyzed. In this document, a "restitution parameter" refers to a cardiac parameter whose restitution is analyzed. Examples of restitution parameters used in the present method and system include action potential duration (APD), conduction velocity (CV), QT interval, and/or T-wave morphology (TM). APD is the duration of the action potential when propagating in cardiac myocytes. CV is the velocity at which an action potential propagates in cardiac myocytes. QT interval is the time interval between ventricular depolarization and repolarization (i.e., between a Q-wave and the subsequently adjacent R-wave on an electrocardiogram or intracardiac electrogram). TM morphology is represented by one or more TM parameters including amplitude and timing parameters measured from a T-wave, such as T-wave amplitude, T-wave width, and a time interval between the peak and the end of a T-wave. Restitution of a cardiac parameter is the functional relationship between that cardiac parameter and the cardiac interval. In one embodiment, the cardiac interval is a diastolic interval measured as the RR interval (time interval between two consecutive R-waves measured from an electrocardiogram or intracardiac electrogram). A restitution curve is a curve of the restitution parameter plotted against the cardiac interval. A restitution curve may be constructed by varying the RR interval, measuring the resulting values of the restitution parameter, and plotting these values of the restitution parameter against the RR interval. In one embodiment, the restitution curve is a line constructed using linear regression. A restitution slope is the slope of the restitution curve, and is the rate of change of the restitution parameter with respect to change in the cardiac interval.

Vagus nerve stimulation (VNS) leads to release of acetylcholine (ACh), which in turn prolongs or shortens APD in a dose-dependent manner. VNS may also act to change arrhythmogenic substrate such that the myocardium is less prone to arrhythmia. The steepness of a restitution curve has been shown to be a reliable indicator of the arrhythmogenicity of the substrate. Thus, in the present method and system, the steepness of a restitution curve, i.e., the restitution slope, is used to indicate efficacy of the neurostimulation, including AMT.

In various embodiments, APD and CV are each approximated by a surrogate, and the APD and/or CV restitution curves are computed using their surrogates. In one embodiment, an APD surrogate includes an activation-recovery interval (ARI) computed from an intracardiac electrogram at one or more locations. In one embodiment, a CV surrogate includes the latency between the observations of a single event at two separate electrogram recording sites. In another embodiment, a CV surrogate includes QRS width measured from an electrogram. In this document, an "APD parameter" includes one or more parameters representing the APD, and a "CV parameter" includes one or more parameters representing the CV. An APD parameter may be directly measured or approximated by a surrogate. A CV parameter may also be directly measured or approximated by a surrogate.

The cardiac interval may also be expressed as heart rate. The RR interval may also be expressed as a ventricular rate, which may be measured as the heart rate of a patient. The relationship between such a "rate" and an "interval" is the relationship between a frequency and its corresponding period. If the heart rate is given in beats per minute (bpm), its corresponding cardiac interval in milliseconds is calculated by dividing 60,000 by the heart rate (where 60,000 is the number of milliseconds in a minute). Any process using a cardiac interval is to be modified accordingly when a heart rate is used instead.

Once produced, a restitution curve or slope is used to guide a neurostimulation therapy for purposes of improving or maintaining a patient's cardiac functions. In various embodiments, one or more restitution curves are used to indicate efficacy of the neurostimulation therapy. The steepness of each of the restitution curves while the neurostimulation therapy is applied to the patient provides a measure of therapy efficacy. In various embodiments, one or more restitution curves are each constructed by linear regression using measured values of one or more cardiac parameters and the associated cardiac intervals. The slope of each cardiac restitution curve is computed and used for adaptive control of the neurostimulation therapy. In various embodiments, the one or more restitution curves are used to form a feedback loop to automatically titrate or modify the neurostimulation therapy as needed.

FIG. 1 is an illustration of an embodiment of a neurostimulation system 100 and portions of an environment in which system 100 is used. In the illustrated embodiment, system 100 includes a neurostimulation circuit 110, a cardiac pacing circuit 114, and a sensing circuit 118. In various embodiments, system 100 includes cardiac pacing circuit 114 only when the patient is treated with cardiac pacing therapy. When available, cardiac pacing circuit 114 may be used to control the cardiac interval for the purpose of analyzing cardiac restitution.

One or more electrodes 111 are electrically connected to neurostimulation circuit 110 through a neural lead 112, and placed on or near a nerve 102 to allow for delivery of neurostimulation from neurostimulation circuit 110 to modulate functions of the patient's heart 101. Nerve 102 represents a nerve of the patient's autonomic nervous system, such as the vagus nerve. One or more electrodes 115 are electrically connected to cardiac pacing circuit 114 through a cardiac lead 116, and placed in or near heart 101 to allow for delivery of pacing pulses from cardiac pacing circuit 114. Sensing circuit 118 senses one or more cardiac signals using electrode(s) 111 and/or electrode(s) 115. In various embodiments when neurostimulation circuit 110 and cardiac pacing circuit 114 are constructed in separate devices, sensing circuit 118 may be constructed as part of neurostimulation circuit 110, part of cardiac pacing circuit 114, or both, depending on the type of the one or more cardiac signals to be sensed. As discussed below, neurostimulation circuit 110 analyzes cardiac restitution using the one or more cardiac signals and controls delivery of the neurostimulation using results of the analysis.

Figure 2:
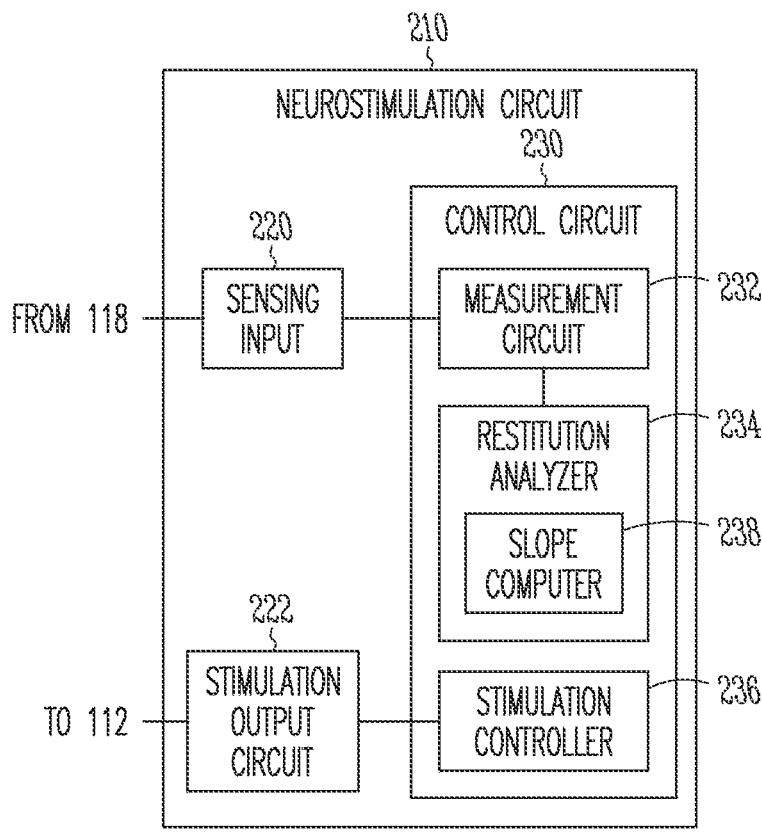
FIG. 2 is a block diagram illustrating an embodiment of a neurostimulation circuit.

FIG. 2 is a block diagram illustrating an embodiment of a neurostimulation circuit 210, which represents an embodiment of neurostimulation circuit 110. Neurostimulation circuit 210 includes a sensing input 220, a stimulation output circuit 222, and a control circuit 230. Sensing input 220 receives one or more cardiac signals from sensing circuit 118. Stimulation output circuit 222 delivers the neurostimulation. In one embodiment, the neurostimulation is in the form of electrical pulses, and stimulation output circuit 222 generates and delivers the electrical pulses. Control circuit 230 includes a measurement circuit 232, a restitution analyzer 234, and a stimulation controller 236. Measurement circuit 232 measures a cardiac interval and a restitution parameter using the one or more cardiac signals. Restitution analyzer 234 analyzes restitution of the restitution parameter and includes a slope computer 238. Slope computer 238 computes a restitution slope using the values of the restitution parameter measured at a plurality of cardiac intervals. The restitution slope is a rate of change of the restitution parameter with respect to change in the cardiac interval. Stimulation controller 236 controls the delivery of the neurostimulation using the restitution slope.

In various embodiments, the one or more cardiac signals sensed by sensing circuit 118 include one or more intracardiac electrograms, one or more subcutaneous electrocardiograms (ECGs), and/or one or more surface ECGs. Electrodes 111 and 115 represent various electrodes allowing for sensing of such one or more cardiac signals. In one embodiment, sensing circuit 118 is programmable for selective connection to electrodes 111 and/or 115 that provides for sensing one or more cardiac signals to allow measurement circuit 232 to perform reliable measurement of parameters. One example of such one or more cardiac signal includes a cardiac signal with a high P-wave amplitude when P-wave is detected for measurement of a restitution parameter. In one embodiment, sensing circuit 118 is programmable for selective connection to electrodes 111 and/or 115 that provides for sensing of two or more cardiac signals to allow measurement circuit 232 to perform reliable measurement of the parameters by signal averaging or averaging of the measured parameters.

In various embodiments, neurostimulation circuit 110, including its various elements discussed in this document, is implemented using a combination of hardware and software. In various embodiments, measurement circuit 232, restitution analyzer 234, and stimulation controller 236, including their various elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 3:
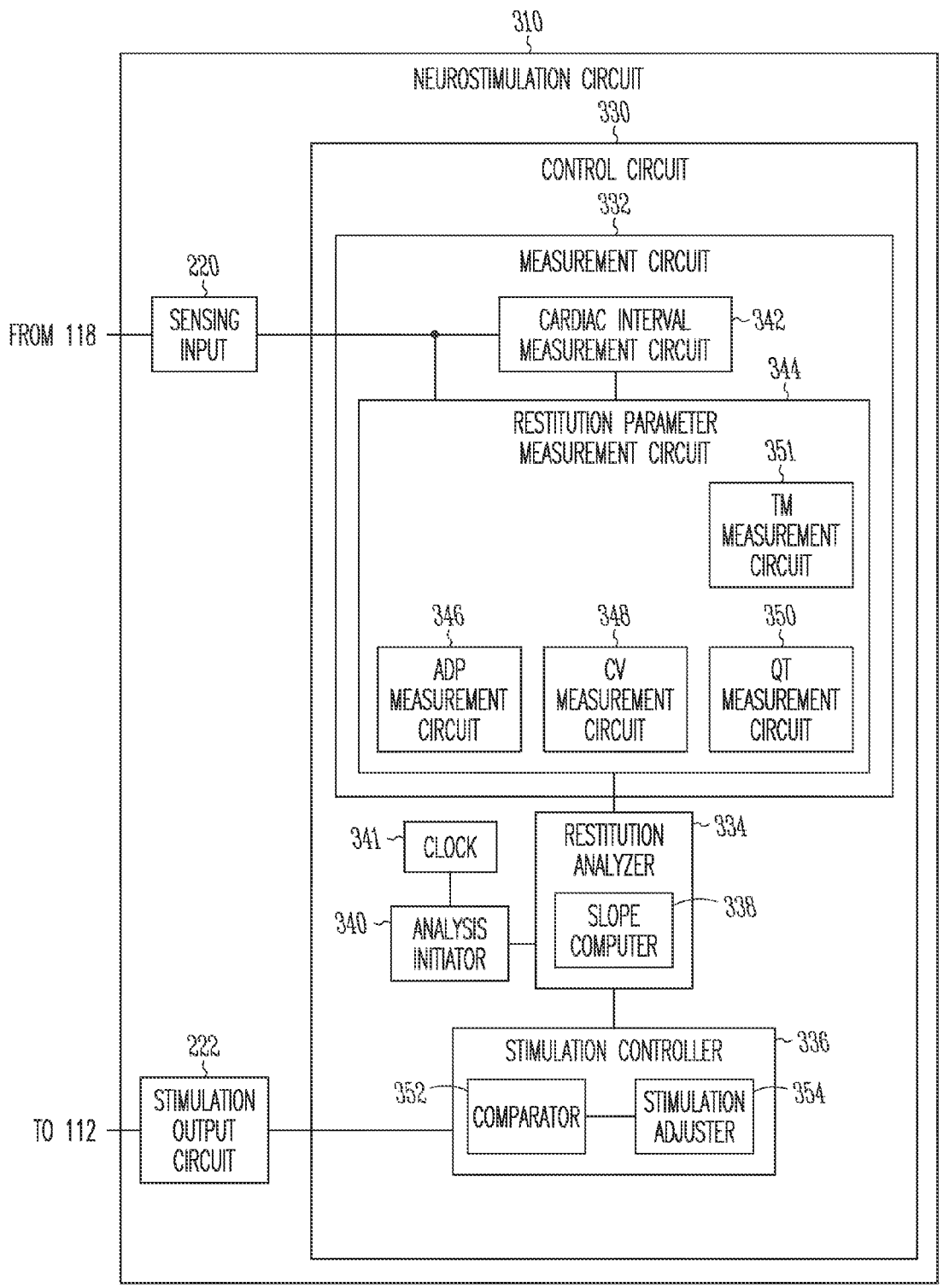
FIG. 3 is a block diagram illustrating another embodiment of the neurostimulation circuit.

FIG. 3 is a block diagram illustrating an embodiment of a neurostimulation circuit 310, which represent another embodiment of neurostimulation circuit 110. Neurostimulation circuit 310 includes sensing input 220, stimulation output circuit 222, and a control circuit 330. Control circuit 330 includes a measurement circuit 332, a restitution analyzer 334, a stimulation controller 336, an analysis initiator 340, and a clock 341.

Measurement circuit 332 represents an embodiment of measurement circuit 232 and includes a cardiac interval measurement circuit 342 and a restitution parameter measurement circuit 344. Cardiac interval measurement circuit 342 measures the cardiac interval using one of the one or more cardiac signals. In one embodiment, cardiac interval measurement circuit 342 measures an RR interval as the cardiac interval using a ventricular electrogram. The RR interval is the time interval between two successive R waves in the ventricular electrogram. Restitution parameter measurement circuit 344 measures values of each of the one or more restitution parameters at a plurality of cardiac intervals. Examples of the one or more restitution parameters include the APD parameter, the CV parameter, the QT interval, and the TM parameter. In various embodiments, restitution parameter measurement circuit 344 measures the one or more restitution parameters each as a directly measured parameter or a measured surrogate. In the illustrated embodiment, restitution parameter measurement circuit 344 includes an APD measurement circuit 346, a CV measurement circuit 348, a QT measurement circuit 350, and a TM measurement circuit 351. In various embodiments, restitution parameter measurement circuit 344 includes APD measurement circuit 346, CV measurement circuit 348, QT measurement circuit 350, TM measurement circuit 351, or any combination of two or three of these circuits.

Figure 4:
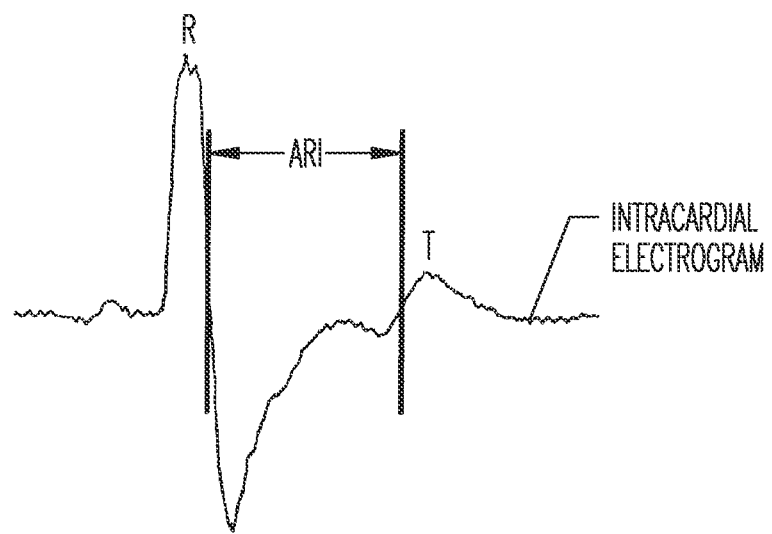
FIG. 4 is an illustration of an embodiment of measuring an action potential duration (APD) parameter from an intracardiac electrogram.

APD measurement circuit 346 measures an APD parameter using the one or more cardiac signals. FIG. 4 is an illustration of an embodiment of measuring an APD parameter from an intracardiac electrogram. In the illustrated embodiment, APD measurement circuit 346 measures an activation-recovery interval (ARI) as the APD parameter using the intracardiac electrogram. The ARI is a time interval between a first point associated with a maximum negative amplitude change (down slope) in an R-wave and a second point associated with a maximum positive amplitude change (up slope) in a T-wave in the intracardiac electrogram.

Figure 5:
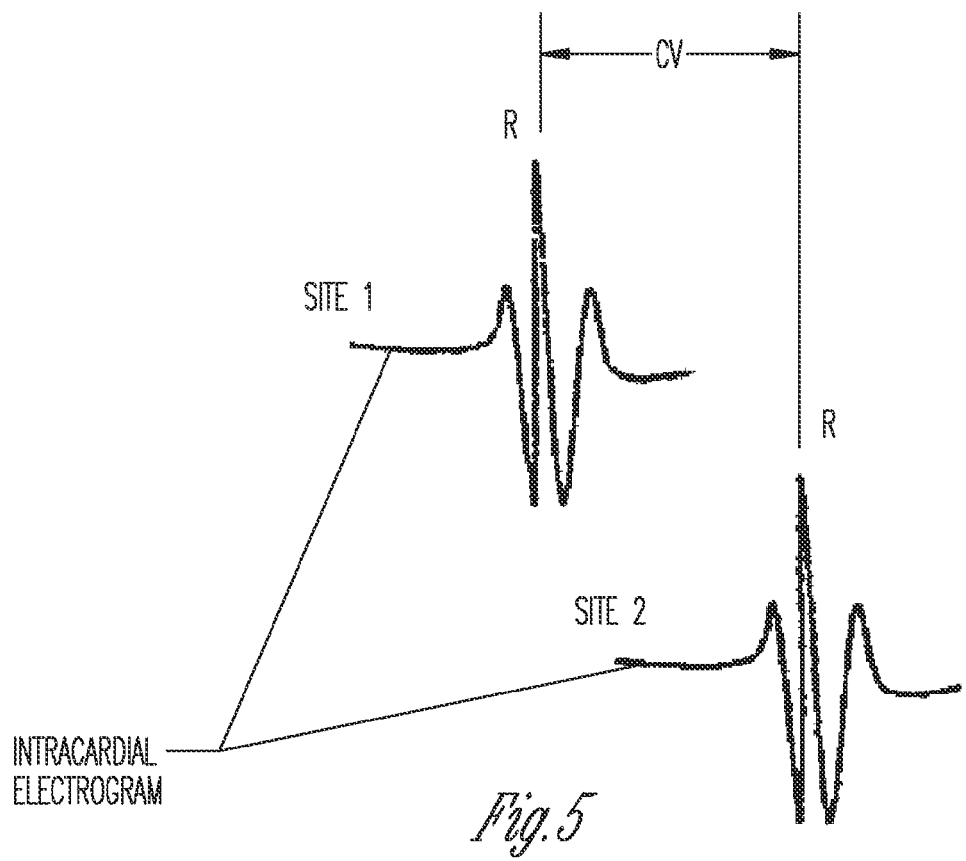
FIG. 5 is an illustration of an embodiment of measuring a conduction velocity (CV) parameter from intracardiac electrograms.
Figure 6:
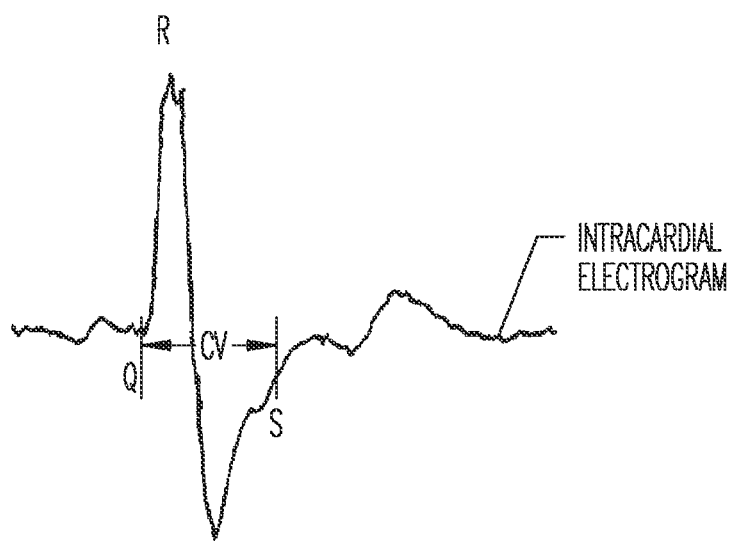
FIG. 6 is an illustration of another embodiment of measuring a CV parameter from an intracardiac electrogram.

CV measurement circuit 348 measures a CV parameter using the one or more cardiac signals. FIG. 5 is an illustration of an embodiment of measuring a CV parameter from intracardiac electrograms. In the illustrated embodiment, CV measurement circuit 348 measures a time interval (CV) between occurrence of a cardiac event in a first intracardiac electrogram and occurrence of the cardiac event in a second intracardiac electrogram. The first and second intracardiac electrograms are sensed using electrodes placed in substantially different sites. In the illustrated embodiment, the cardiac event is an R-wave. FIG. 6 is an illustration of another embodiment of measuring the CV parameter from an intracardiac electrogram. In the illustrated embodiment, CV measurement circuit 348 measures a QRS width as the CV parameter (CV) from the intracardiac electrogram.

Figure 7:
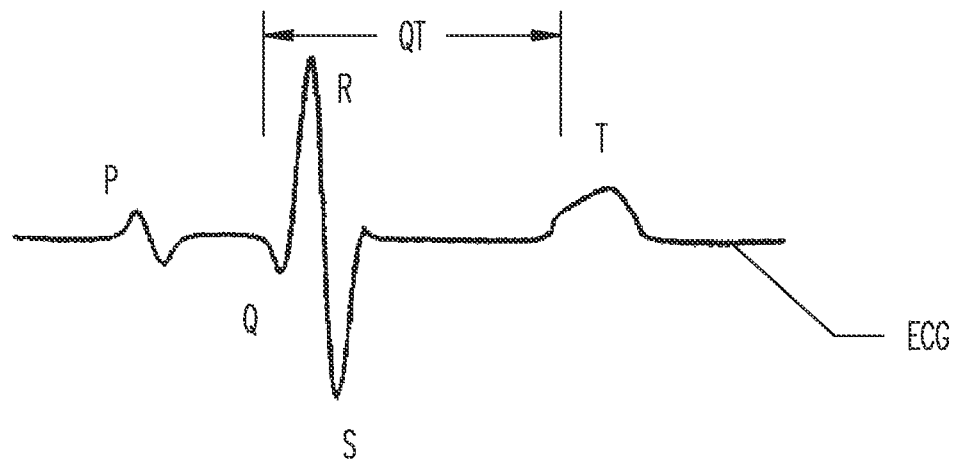
FIG. 7 is an illustration of an embodiment of measuring a QT interval (QT) from a small vector electrocardiogram (ECG).

QT measurement circuit 350 measures a QT interval using the one or more cardiac signals. In one embodiment, a small vector ECG is measured using electrodes on the housing of an implantable medical device and/or one or more neural leads connected to the implantable medical device. FIG. 7 is an illustration of an embodiment of measuring a QT interval from a small vector ECG. In another embodiment, QT measurement circuit 350 measures the QT interval using a surface ECG signal. In the illustrated embodiment, QT measurement circuit 350 measures the QT interval being a time interval between the Q-wave and the subsequent T-wave in a cardiac cycle.

Figure 8:
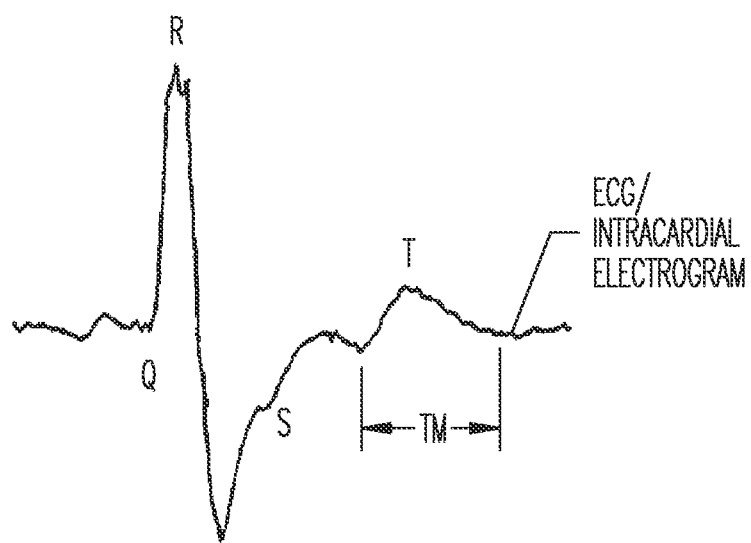
FIG. 8 is an illustration of an embodiment of measuring a T-wave morphology (TM) parameter from an intracardiac electrogram or ECG.
Figure 9:
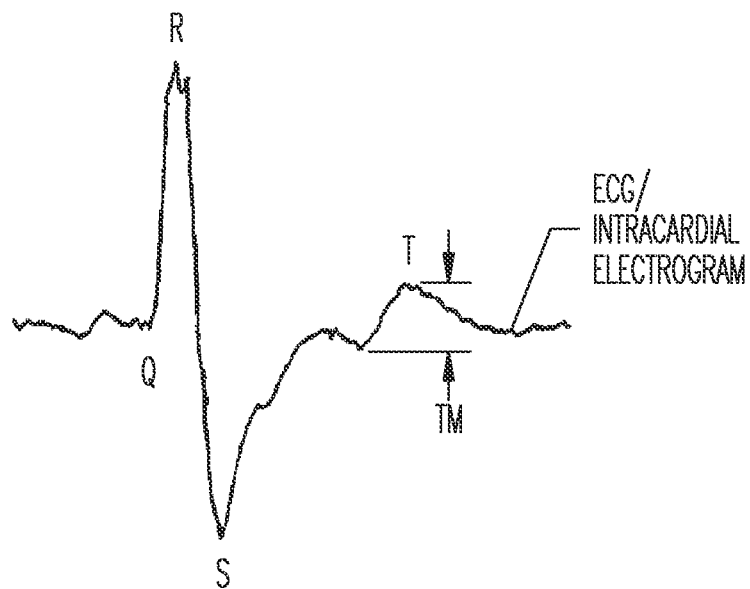
FIG. 9 is an illustration of another embodiment of measuring a TM parameter from an intracardiac electrogram or ECG.
Figure 10:
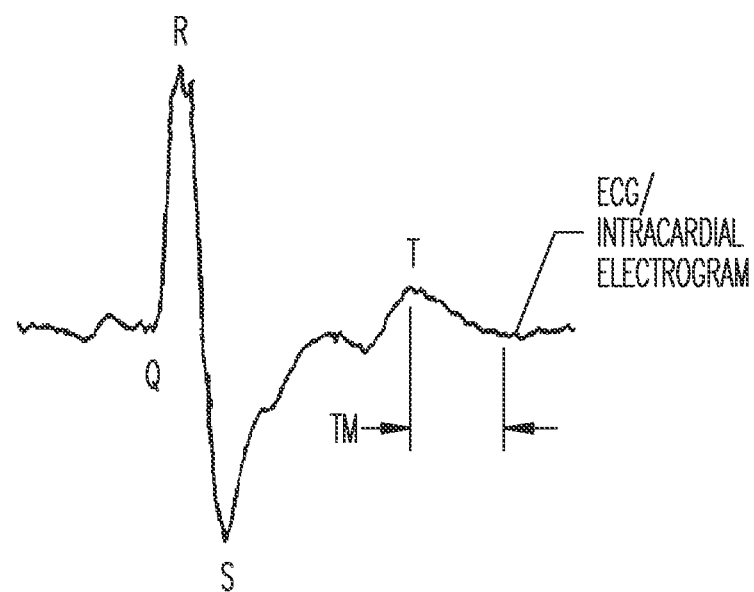
FIG. 10 is an illustration of another embodiment of measuring a TM parameter from an intracardiac electrogram or ECG.

TM measurement circuit 351 measures a TM parameter using the one or more cardiac signals. FIG. 8 is an illustration of an embodiment of measuring a TM parameter from an intracardiac electrogram, subcutaneous ECG, or surface ECG. In the illustrated embodiment, TM measurement circuit 351 measures an amplitude of a T-wave, such as the voltage of the peak of the T-wave. FIG. 9 is an illustration of another embodiment of measuring the TM parameter using the one or more cardiac signals. In the illustrated embodiment, TM measurement circuit 351 measures a width of a T-wave, such as the time interval during which the T-wave amplitude exceeds a specified threshold. FIG. 10 is an illustration of another embodiment of measuring the TM parameter using the one or more cardiac signals. In the illustrated embodiment, TM measurement circuit 351 measures a time interval between the peak and the end of a T-wave. In one embodiment, the end of the T-wave occurs when the T-wave amplitudes fails below a specified threshold.

Figure 11:
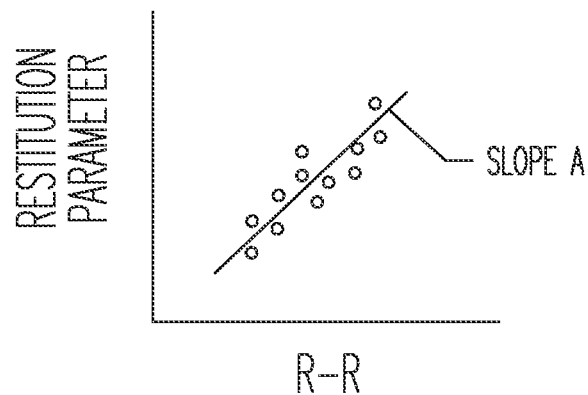
FIGS. 11 and 12 are illustrations of restitution curves.
Figure 12:
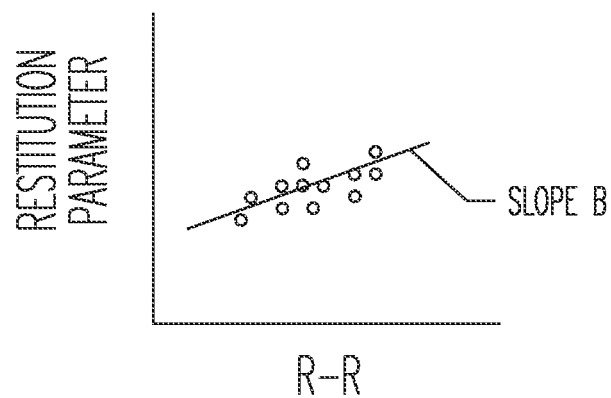

FIGS. 11 and 12 are illustrations of restitution curves obtained by linear regression using the restitution parameter values measured at a range of different RR intervals. For illustration purposes, the restitution parameter in FIGS. 11 and 12 represents any of the APD parameter, the CV parameter, the QT interval, and the TM parameter illustrated in FIGS. 4-10 as well as any other restitution parameter suitable for the restitution analysis as discussed in this document. The restitution curves have substantially different slopes A and B. Slopes A and B are each a restitution slope being a rate of change of the restitution parameter with respect to change in the RR interval. In various embodiments, slopes A and B each represent an APD restitution slope being a rate of change of the APD parameter with respect to change in the RR interval, a CV restitution slope being a rate of change of the CV parameter with respect to change in the RR interval, a QT restitution slope being a rate of change of the QT interval with respect to change in the RR interval, or a TM restitution slope being a rate of change of the TM parameter with respect to change in the RR interval.

Restitution analyzer 334 represents an embodiment of restitution analyzer 234 and includes a slope computer 338, which represents an embodiment of slope computer 238. In the illustrated embodiment, restitution analyzer 334 analyzes restitution of each of the APD parameter, CV parameter, QT interval, and TM parameter, and slope computer 338 compute each of the APD restitution slope, the CV restitution slope, the QT restitution slope, and the TM restitution slope. In various embodiments, restitution analyzer 334 analyzes restitution of each of one or more of the APD parameter, CV parameter, QT interval, or TM parameter, and slope computer 338 computes each of one or more of the APD restitution slope, the CV restitution slope, the QT restitution slope, or the TM restitution slope. In one embodiment, as illustrated in FIGS. 11 and 12, slope computer 338 computes each restitution slope using linear regression. The restitution slope is a slope of a restitution curve resulting from linear regression of the measured values of the restitution parameter plotted against the plurality of values of the cardiac interval.

Stimulation controller 336 represents an embodiment of stimulation controller 236 and controls the delivery of the neurostimulation using one or more restitution slopes provided by slope computer 338. In various embodiments, stimulation controller 336 controls the delivery of the neurostimulation with stimulation parameters programmed for treating one or more cardiovascular disorders. Examples of the one or more cardiovascular disorders include heart failure, atrial and ventricular arrhythmias, myocardial infarction (including post-myocardial infarction disorders), renal failure, hypertension, and syncope. In various embodiments, stimulation controller 336 determines whether each computed restitution slope is within a specified target range, and adjusts the stimulation parameters using an outcome of the determination. Stimulation controller 336 includes a comparator 352 and a stimulation adjuster 354. Comparator 352 compares each restitution slope to the specified target range, which includes one or more thresholds. Stimulation adjuster 354 adjusts the delivery of the neurostimulation using an outcome of the comparison. In one embodiment, a restitution slope being within the specified target range when neurostimulation is being delivered indicates that the neurostimulation has been effective or that the patient does not need neurostimulation. Thus, stimulation adjuster 354 stops or maintains the delivery of the neurostimulation in response to the restitution slope being within the specified target range. A restitution slope being outside the specified target range when the neurostimulation is being delivered indicates that the neurostimulation has not been effective. Thus, stimulation adjuster 354 adjusts the stimulation parameters in response to the computed restitution slope being outside the specified target range. A restitution slope being outside the specified target range when the neurostimulation is not being delivered indicates that the patient needs neurostimulation. Thus, stimulation adjuster 354 starts the delivery of the neurostimulation in response to the computed restitution slope being outside the specified target range.

In various embodiments when multiple restitution parameters are analyzed, measurement circuit 332 measures the cardiac interval and the multiple restitution parameters using the sensed one or more cardiac signals, restitution analyzer 334 computes multiple restitution slopes each being the rate of change of one of the multiple restitution parameters with respect to the change in the cardiac interval, and stimulation controller 336 controls the delivery of the neurostimulation using the multiple restitution slopes. In one embodiment, the target range for the multiple restitution parameters includes a sub-target range for each slope of the multiple restitution slopes. The sub-target range includes one or more thresholds. Comparator 352 compares the each slope to its sub-target range, and determines whether the restitution slopes are within the specified target range by using a weighted sum of results of the comparisons.

Analysis initiator 340 initiates a restitution analysis by restitution analyzer 334. Each restitution analysis includes computation of one or more restitution slopes. Stimulation adjuster 354 adjusts the delivery of the neurostimulation in response to each computation of the restitution slope that results in a need for adjustment. In various embodiments, analysis initiator 340 initiates the restitution analysis according to a specified schedule, such as on a periodic basis. Clock 341 times the specified schedule. In one embodiment, analysis initiator 340 initiates the restitution analysis at a specified time each day. In another embodiment, analysis initiator 340 initiates the restitution analysis at a period of approximately 21 hours. This 21-hour period allows the restitution analysis to approximately cover each stage in the circadian rhythm of the patient in a week. In various other embodiments, analysis initiator 340 detects a specified type triggering event and initiates the restitution analysis in response to a detection of the specified type triggering event. In one embodiment, the specified type triggering event indicates an onset of a period during which the patient's cardiac interval is expected to vary substantially, thus allowing for the restitution analysis. Examples of such a triggering event include a signal from the patient indicating the beginning of an exercise and a signal from control circuit 330 or other device indicating the beginning of a stimulation sequence during which the patient's cardiac interval is controlled to provide the range of cardiac intervals required for the restitution analysis. In one embodiment, the stimulation sequence is a cardiac pacing sequence. In another embodiment, the stimulation sequence is a neurostimulation sequence.

Figure 13:
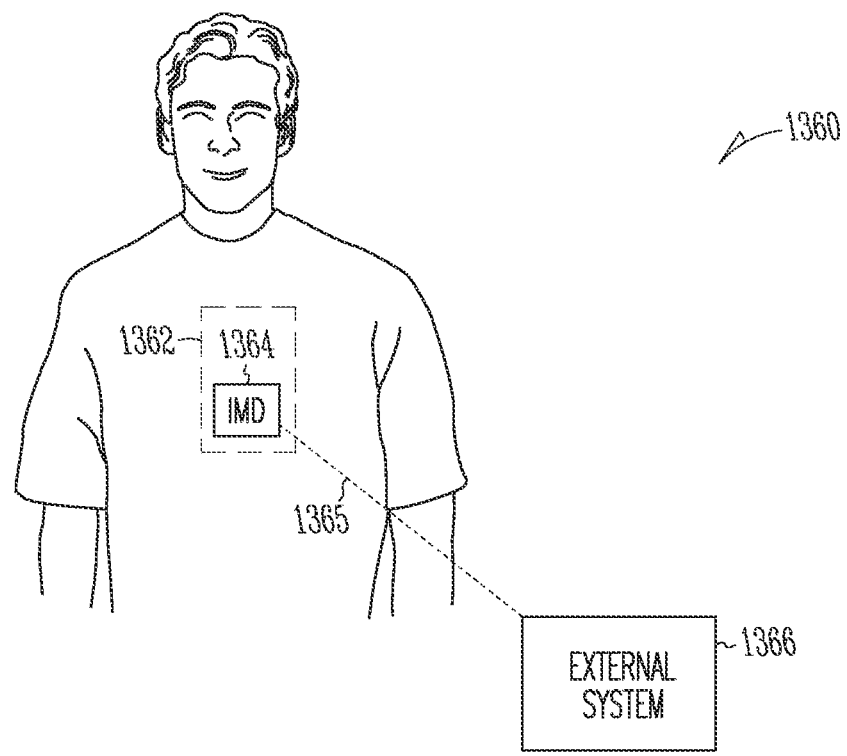
FIG. 13 is an illustration of an embodiment of an implantable system including the neurostimulation circuit and portions of an environment in which the implantable system is used.

FIG. 13 is an illustration of an embodiment of an implantable system 1360 including neurostimulation circuit 110 (including its various embodiments) and portions of an environment in which implantable system 1360 is used. In one embodiment, system 1360 includes system 100 including its various embodiments as discussed in this document.

System 1360 includes an implantable system 1362 and an external system 1366. Implantable system 1362 includes an implantable medical device (IMD) 1364. External system 1366 and IMD 1364 communicate via a telemetry link 1365. In various embodiments, IMD 1364 is a neurostimulator including neurostimulation circuit 110, including its various embodiments. In various embodiments, IMD 1364 integrates a cardiac rhythm management (CRM) device with a neural sensing and stimulation device and thus includes portions of system 100, including its various embodiments. The CRM device senses cardiac electrical activities and delivers cardiac pacing pulses. Examples of the CRM device include pacemakers, cardioverter/defibrillators, combined pacemaker-cardioverter/defibrillators, cardiac resynchronization therapy (CRT) devices, and cardiac remodeling control therapy (RCT) devices. In various embodiments, neural activities are sensed to indicate a need for cardiac stimulation and/or to control the timing of pacing pulse deliveries. In various embodiments, cardiac activities are sensed to control the timing of neural stimulation pulse deliveries, such as to synchronize neural stimulation to cardiac cycles.

Figure 14:
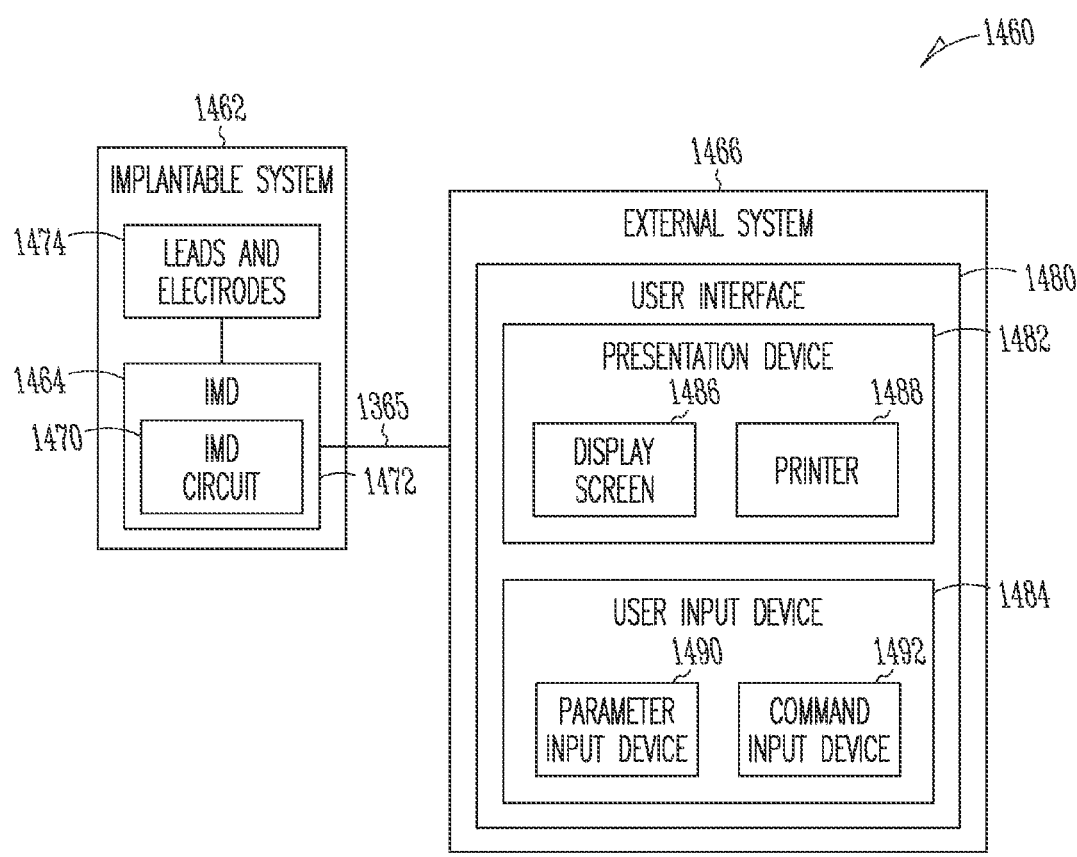
FIG. 14 is a block diagram illustrating an embodiment of the implantable system of FIG. 13.

FIG. 14 is a block diagram illustrating an embodiment of an implantable system 1460. System 1460 represents an embodiment of system 1360 and includes an implantable system 1462 and an external system 1466.

Implantable system 1462 represents an embodiment of implantable system 1362 and includes leads and electrodes 1474, and an IMD 1464. Leads and electrodes 1474 allow for delivery of the neurostimulation, and optionally cardiac pacing from IMD 1464. IMD 1464 represents an embodiment of IMD 1364 and includes an IMD circuit 1470 and an implantable housing 1472 encapsulating IMD circuit 1470. In one embodiment, IMD circuit 1470 includes neurostimulation circuit 110, 210, or 310. In another embodiment, IMD circuit 1470 further includes cardiac pacing circuit 114 and/or sensing circuit 118. In various embodiments, electrodes are incorporated onto one or more leads and/or implantable housing 1472. In one embodiment, leads and electrodes 1474 includes intracardiac leads for sensing intracardiac electrograms such as the ventricular electrograms discussed in this document. In one embodiment, leads and electrodes 1474 includes electrodes on the housing of the implantable neurostimulator and/or one or more neurostimulation leads for sensing the small vector ECG discussed in this document. External system 1466 is an embodiment of external system 1366 and is communicatively coupled to IMD 1464 via telemetry link 1365. External system 1466 includes a user interface 1480. User interface 1480 includes a presentation device 1482 and a user input device 1484. Presentation device 1482 presents, for example, signals and parameters used for the restitution analysis and results of the restitution analysis. In the illustrated embodiment, presentation device 1482 includes a display screen 1486 and a printer 1488. User input device 1484 includes a parameter input device 1490 and a command input device 1492. Parameter input device 1490 allows a user to adjust the stimulation parameters. In one embodiment, parameter input device 1490 also allows the user to select one or more restitution parameters for the restitution analysis. Command input device 1492 allows the user to enter commands controlling the operation of system 1460, such as a command for initiating the restitution analysis and a subsequent adjustment of the neurostimulation.

In one embodiment, external system 1466 includes a programmer including user interface 1480. In one embodiment, external system 1466 includes a patient management system including an external device communicatively coupled to IMD 1464 via telemetry link 1365 and a remote device in a distant location and communicatively coupled to the external device via a communication network. The external device and/or the remote device include user interface 1480.

Figure 15:
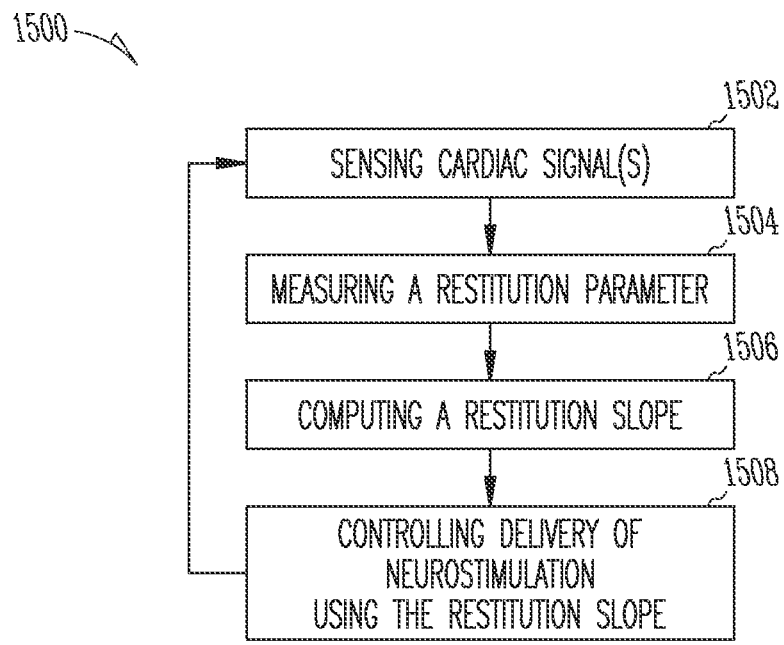
FIG. 15 is a flow chart illustrating an embodiment of a method for controlling neurostimulation using cardiac restitution.

FIG. 15 is a flow chart illustrating an embodiment of a method 1500 for controlling neurostimulation using cardiac restitution. In one embodiment, method 1500 is performed using system 100, including its various embodiments discussed in this document.

At 1502, one or more cardiac signals are sensed from a patient. At 1504, a restitution parameter is measured using the sensed one or more cardiac signals at a plurality of cardiac intervals. Examples of the restitution parameter include the APD parameter, the CV parameter, the QT interval, and the TM parameter as discussed above. The plurality of cardiac intervals covers a specified range of cardiac intervals. In one embodiment, the patient's intrinsic RR interval is measured as the cardiac interval using one of the sensed one or more cardiac signals. In another embodiment, the cardiac intervals are controlled by delivering cardiac pacing pulses to the patient. At 1506, a restitution slope is computed using the values of the restitution parameter measured at the plurality of cardiac intervals. The restitution slope is a rate of change of the restitution parameter with respect to change in the cardiac interval. At 1508, delivery of the neurostimulation is controlled using the restitution slope.

Figure 16:
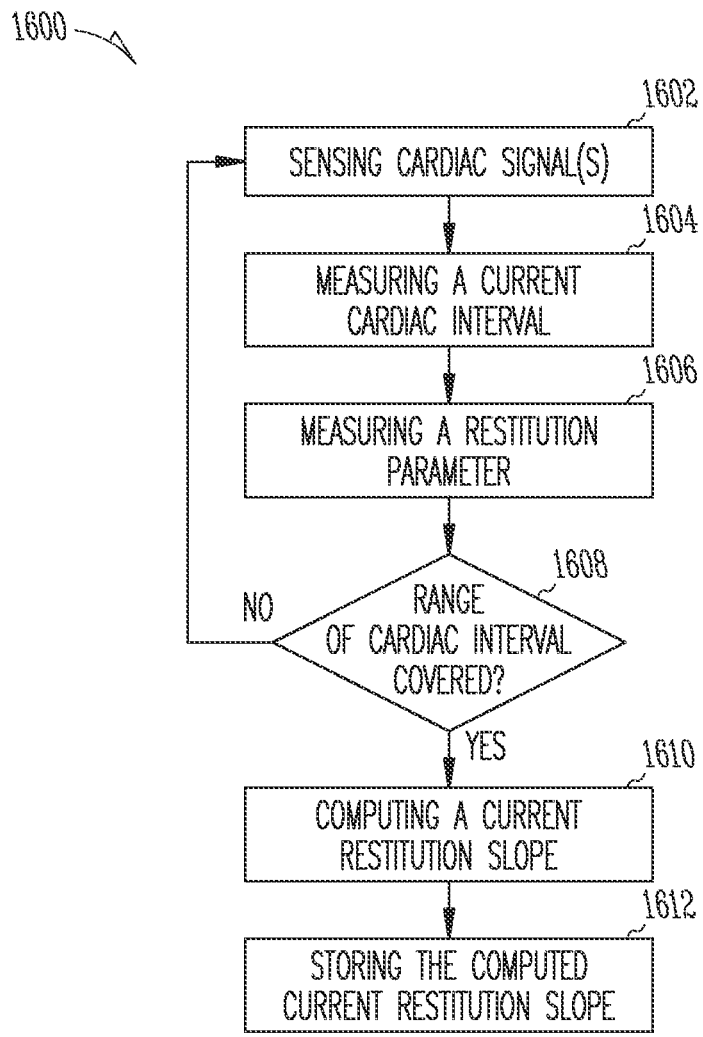
FIG. 16 is a flow chart illustrating an embodiment of a method for analyzing cardiac restitution using intrinsic cardiac intervals.
Figure 17:
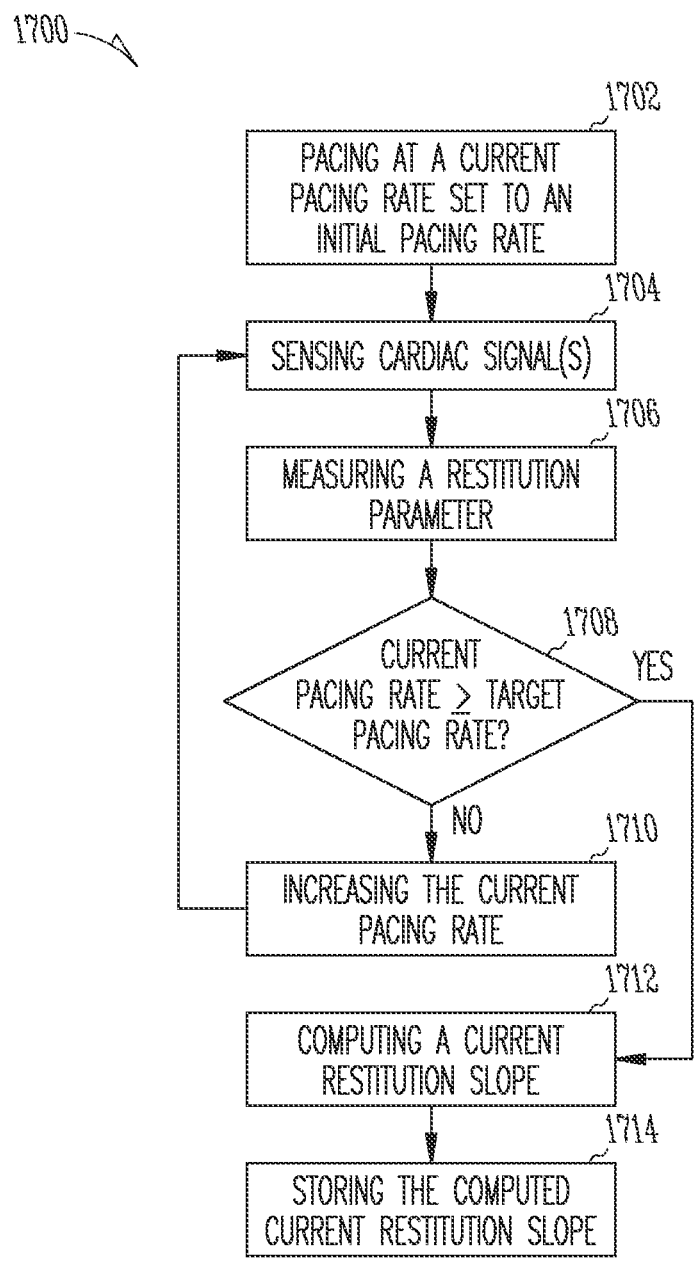
FIG. 17 is a flow chart illustrating an embodiment of a method for analyzing cardiac restitution using paced cardiac intervals.
Figure 18:
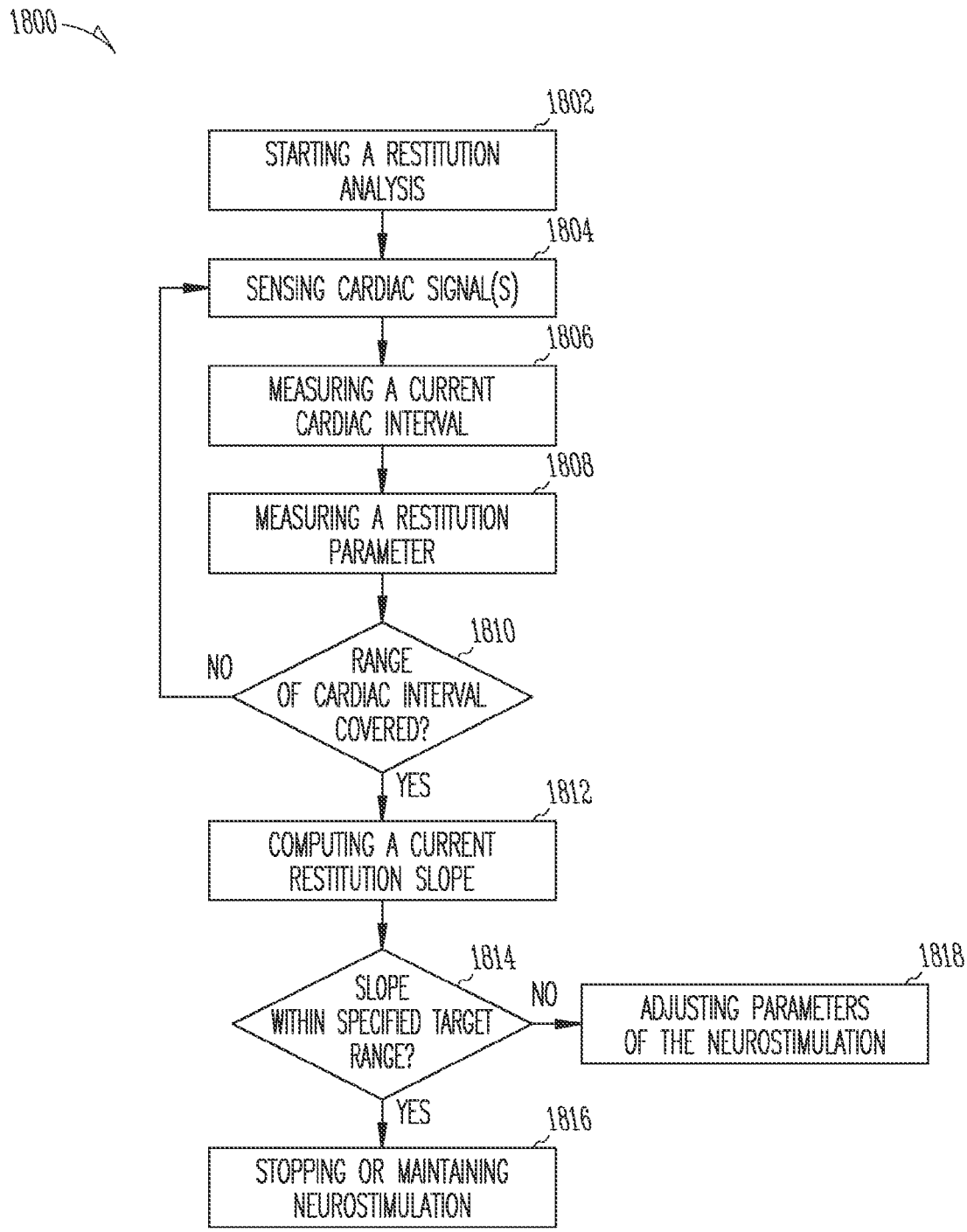
FIG. 18 is a flow chart illustrating an embodiment of a method for controlling neurostimulation using cardiac restitution analyzed using intrinsic cardiac intervals.
Figure 19:
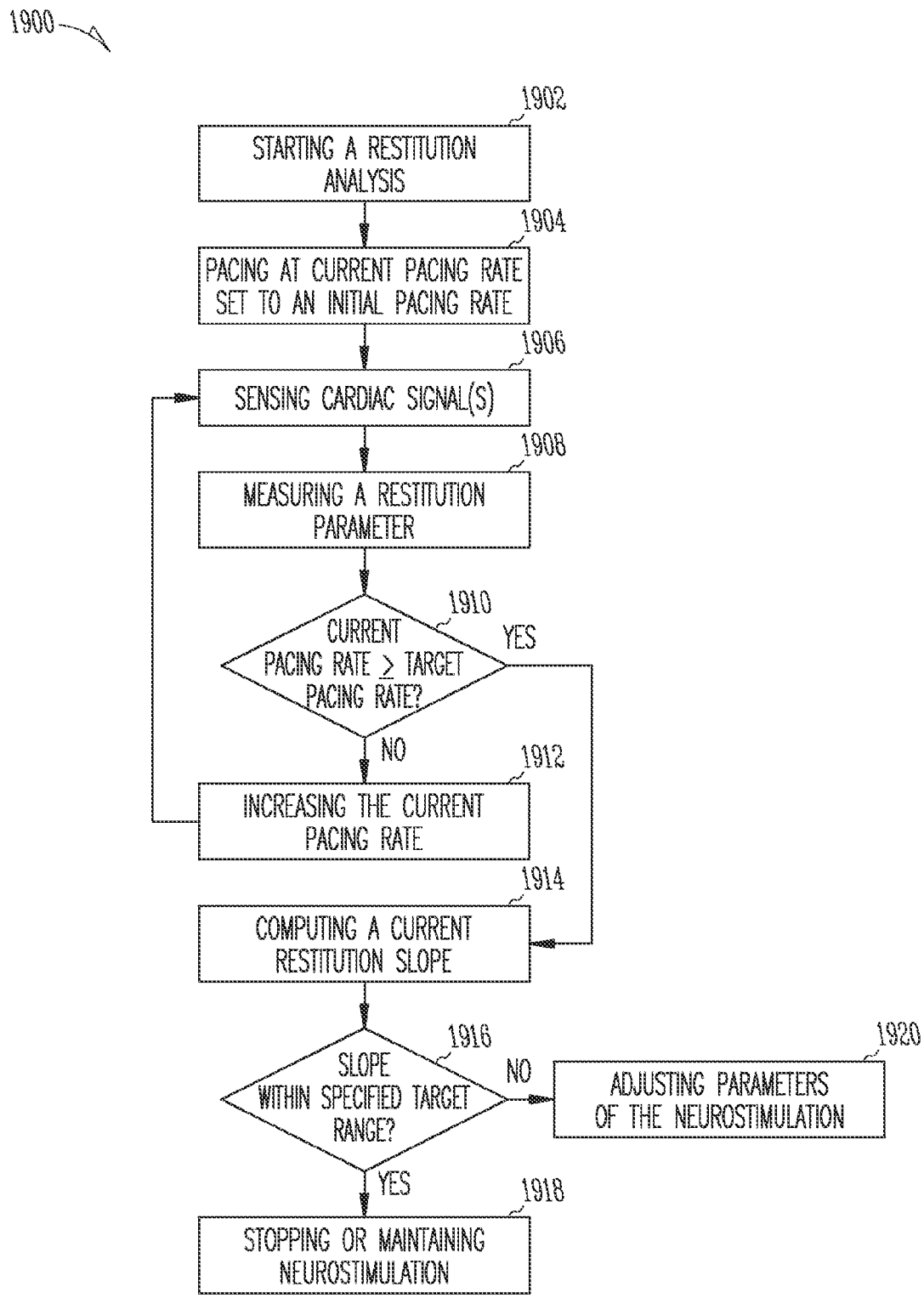
FIG. 19 is a flow chart illustrating an embodiment of a method for controlling neurostimulation using cardiac restitution analyzed using paced cardiac intervals.

FIGS. 16-19 illustrate methods representing specific embodiments of method 1500 or part thereof. FIGS. 16 and 17 illustrate methods for analyzing cardiac restitution for the patient, including computing a restitution slope for a restitution parameter. FIGS. 18 and 19 illustrate methods for controlling delivery of neurostimulation such as AMT to the patient using an outcome of the analysis of cardiac restitution. In one embodiment, the methods illustrated in FIGS. 16-19 are performed using system 100, including its various embodiments discussed in this document.

FIG. 16 is a flow chart illustrating an embodiment of a method 1600 for analyzing cardiac restitution using intrinsic cardiac intervals. At 1602, one or more cardiac signals are sensed. At 1604, a current cardiac interval is measured. At 1606, a restitution parameter is measured using the sensed one or more cardiac signals for the current cardiac interval. At 1608, whether a specified range of cardiac interval has been covered is determined. If the specified range of cardiac interval has not been covered, steps 1602, 1604, 1606, and 1608 are repeated. If the specified range of cardiac interval has been covered, at 1610, a current restitution slope is computed using the values of the restitution parameter measured at the measured cardiac intervals. At 1612, the computed current restitution slope is stored.

FIG. 17 is a flow chart illustrating an embodiment of a method 1700 for analyzing cardiac restitution using paced cardiac intervals. Method 1700 may be used when method 1600 cannot be performed satisfactorily because values of the patient's intrinsic cardiac interval do not cover the specified range, and when cardiac pacing is available for delivering to the patient. At 1702, the patient is paced at a current pacing rate set to a specified initial pacing rate. At 1704, one or more cardiac signals are sensed. At 1706, a restitution parameter is measured using the sensed one or more cardiac signals for the current pacing rate. At 1708, the current pacing rate is compared to a target pacing rate. If the current pacing rate does not exceed the target rate, at 1710, the current pacing rate is increased by a specified increment, and then steps 1704, 1706, and 1708 are repeated. This allows the specified range of cardiac interval to be covered by various pacing rates. If the current rate exceeds the target rate, at 1712, a current restitution slope is computed using the measured restitution parameter. At 1714, the computed current restitution slope is stored.

FIG. 18 is a flow chart illustrating an embodiment of a method 1800 for controlling neurostimulation using cardiac restitution analyzed using intrinsic cardiac intervals. At 1802, a restitution analysis is started according to a specified schedule, such as on a periodic basis. This allows the neurostimulation to be adjusted using feedback control based on the analysis of cardiac restitution. At 1804, one or more cardiac signals are sensed. At 1806, a current cardiac interval is measured using one of the sensed one or more cardiac signals. At 1808, a restitution parameter is measured for the current cardiac interval using the sensed one or more cardiac signals. At 1810, whether a specified range of cardiac interval has been covered is determined. If the specified range of cardiac interval has not been covered, steps 1804, 1806, 1808, and 1810 are repeated. If the specified range of cardiac interval has been covered, at 1812, a current restitution slope is computed using the measured restitution parameter. At 1814, whether the computed restitution slope is within a specified target range is determined. If the computed restitution slope is within a specified target range, at 1816, delivery of the neurostimulation is stopped (when the computed restitution slope is considered to indicate that the patient does not need additional neurostimulation, for example) or maintained (when the computed restitution slope is considered to indicate that the neurostimulation is effective, for example). If the computed restitution slope is not within a specified target range, at 1818, one or more stimulation parameters for the neurostimulation are adjusted (to increase intensity of the neurostimulation, for example). Examples of the one or more stimulation parameters include pulse amplitude, pulse width, pulse frequency or inter-pulse interval, duty cycle, waveform (e.g., monophasic or biphasic), polarity, and ramping (rate of increase or decrease in the amplitude).

FIG. 19 is a flow chart illustrating an embodiment of a method 1900 for controlling neurostimulation using cardiac restitution analyzed using paced cardiac intervals. Method 1900 may be used when method 1800 cannot be performed satisfactorily because values of the patient's intrinsic cardiac interval do not cover the specified range, and when cardiac pacing is available for delivering to the patient. At 1902, a restitution analysis is started according to a specified schedule, such as on a periodic basis. This allows the neurostimulation to be adjusted using feedback control based on the analysis of cardiac restitution. At 1904, the patient is paced at a current pacing rate set to a specified initial pacing rate. At 1906, one or more cardiac signals are sensed. At 1908, a restitution parameter is measured using the sensed one or more cardiac signals for the current pacing rate. At 1910, the current pacing rate is compared to a target pacing rate. If the current pacing rate does not exceed the target rate, at 1912, the current pacing rate is increased by a specified increment, and then steps 1906, 1908, and 1910 are repeated. This allows the specified range of cardiac interval to be covered by various pacing rates. If the current rate exceeds the target rate, at 1914, a current restitution slope is computed using the measured restitution parameter. At 1916, whether the computed restitution slope is within a specified target range is determined. If the computed restitution slope is within a specified target range, at 1918, delivery of the neurostimulation is stopped (when the computed restitution slope is considered to indicate that the patient does not need additional neurostimulation, for example) or maintained (when the computed restitution slope is considered to indicate that the neurostimulation is effective, for example). If the computed restitution slope is not within a specified target range, at 1920, one or more stimulation parameters for the neurostimulation are adjusted (to increase intensity of the neurostimulation, for example). Examples of the one or more stimulation parameters include pulse amplitude, pulse width, pulse frequency or inter-pulse interval, duty cycle, waveform (e.g., monophasic or biphasic), polarity, and ramping (rate of increase or decrease in the amplitude).

Examples of the restitution parameter in each of methods 1500, 1600, 1700, 1800, and 1900 include the APD parameter, the CV parameter, the QT interval, and the TM parameter as discussed above. While one restitution parameter is discussed as an example of each of methods 1500, 1600, 1700, 1800, and 1900, in various embodiments of these methods, one or more restitution parameters including the APD parameter, the CV parameter, the QT parameter, and/or the TM parameter are measured and analyzed, resulting in one or more restitution slopes. The delivery of the neurostimulation is controlled using the one or more restitution slopes.

In one embodiment, multiple restitution parameters are measured, and multiple restitution slopes are computed. The target range for the multiple restitution slopes includes sub-target ranges each including one or more thresholds for one of the multiple computed restitution slopes. Each of the multiple restitution slopes is compared to its sub-target range. In one embodiment of step 1814 or 1916, the computed restitution slopes are within the specified target range when each of the multiple restitution slopes is within its sub-target range. In another embodiment of step 1814 or 1916, the computed restitution slopes are each compared to its sub-target range, and whether the computed restitution slopes are within the specified target range is determined by using a weighted sum of results of the comparisons.

Figure 20:
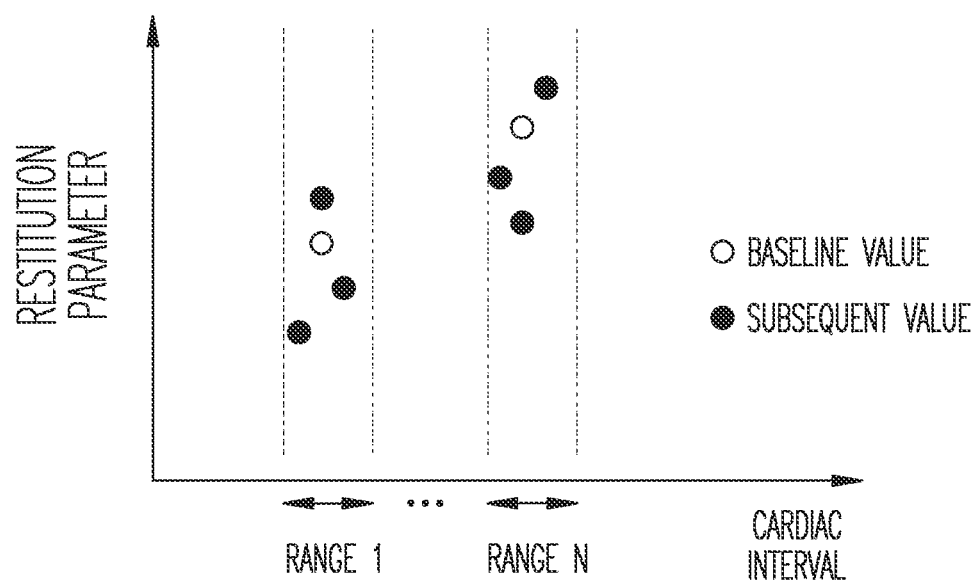
FIG. 20 is an illustration of restitution parameter values monitored for specified cardiac interval ranges.

FIG. 20 is an illustration of restitution parameter values monitored for specified cardiac interval ranges. In one embodiment, values of a restitution parameter are monitored for the purpose of adjusting the delivery of the neurostimulation, including starting, stopping, and maintaining the delivery of the neurostimulation and adjusting one or more stimulation parameters controlling the neurostimulation. Examples of the restitution parameter include the APD parameter, the CV parameter, the QT interval, and the TM parameter. The values of the monitored restitution parameter and other parameters associated with the values of the monitored restitution parameter are stored to be used for adjusting the delivery of the neurostimulation. In various embodiments, values of two or more restitution parameters are monitored, stored, and used adjusting the delivery of the neurostimulation.

In an example as illustrated in FIG. 20, the restitution parameter is monitored for specified ranges (RANGES 1 . . . N) of the cardiac interval. In one embodiment, restitution parameter measurement circuit 344 measures the restitution parameter for each of the specified range 1 to N of the cardiac interval when the patient's cardiac interval falls into that specified range. The measured values, including baseline values (measured on "day 1") and subsequent values (measured after "day 1") as illustrated in FIG. 20, as well as the associated values of the stimulation parameters at the time of measurement, are stored in control circuit 330. In one embodiment, restitution parameter measurement circuit 344 measures and stores the baseline and/or subsequent values of the restitution parameter during the performance of methods 1500, 1600, 1700, 1800, or 1900. In various embodiments, stimulation controller 336 uses the stored values of the restitution parameter to control the delivery of the neurostimulation. In one embodiment, stimulation adjuster 354 adjusts the delivery of the neurostimulation for a specified target value or value range of the restitution parameter. For example, for a specified range of the cardiac interval, if the restitution parameter has an undesirable value or changes in an undesirable direction when the neurostimulation is not being delivered, stimulation adjuster 354 starts the delivery of the neurostimulation. In another example, if the restitution parameter changes in a desirable direction but does not reach a desirable target value or value range when the neurostimulation is being delivered, stimulation adjuster 354 adjusts the stimulation parameters to change the intensity of the neurostimulation. In another embodiment, stimulation controller 336 adjusts the delivery of the neurostimulation in conjunction with the restitution analysis. For example, stimulation controller 336 performs steps 1818 of method 1800 or 1920 of method 1900 by adjusting the stimulation parameters for a specified target value or value range of the measured restitution parameter that correspond to the specified restitution slope. The stored values of the restitution parameter, each associated with a value or value range of the cardiac interval and values of stimulation parameters, provide for mapping of the stimulation parameters to a desirable value or value range of the restitution parameter. In one embodiment, stimulation adjustor 354 adjusts the stimulation parameters using this mapping. In various embodiments, examples of the stimulation parameters adjusted by stimulation adjuster 354 using the measured values of the restitution parameter include pulse amplitude, pulse width, pulse frequency or inter-pulse interval, duty cycle, waveform (e.g., monophasic or biphasic), polarity, ramping (rate of increase or decrease in the amplitude), and stimulation duration (e.g., daily dose or periodic dose specified as duration of therapy session).

Figure 21:
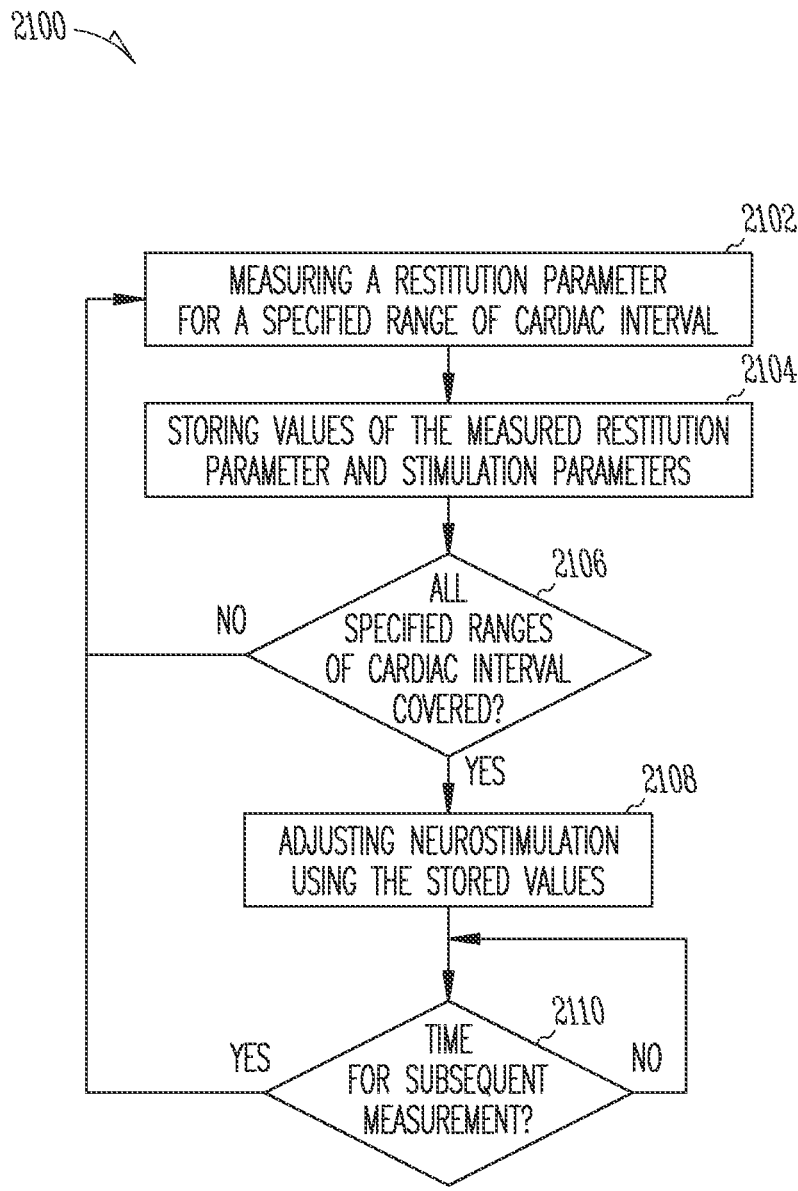
FIG. 21 is a flow chart illustrating an embodiment of a method for adjusting neurostimulation using the restitution parameter values monitored for the specified cardiac interval ranges.

FIG. 21 is a flow chart illustrating an embodiment of a method 2100 for adjusting neurostimulation using the restitution parameter values monitored for the specified cardiac interval ranges. In one embodiment, method 1500 is performed using system 100, including its various embodiments discussed in this document. Examples of the restitution parameter include the APD parameter, the CV parameter, the QT interval, and the TM parameter. In various embodiments, adjusting the neurostimulation includes starting, stopping, and maintaining delivery of the neurostimulation and adjusting one or more stimulation parameters controlling the neurostimulation. While one restitution parameter is specifically discussed as an example, in various embodiments, values of two or more restitution parameters may be monitored and used adjusting the delivery of the neurostimulation. In various embodiments, method 2100 is performed independently or in conjunction with methods 1800 or 1900 as steps 1818 or 1920, respectively.

At 2102, the restitution parameter is measured for a specified range of the patient's cardiac interval. In one embodiment, the restitution parameter is measured when the patient's intrinsic cardiac interval falls into the specified range. In another embodiment, the restitution parameter is measured when the patient's cardiac interval falls into the specified range in response to cardiac pacing or neurostimulation. At 2104, the measured value of the restitution parameter is stored, together with values of the stimulation parameters at the time of the measurement, for the specified range of the patient's cardiac interval. Steps 2102 and 2104 are repeated until all the specified ranges of the cardiac interval are covered at 2106. This results in a set of values and/or value ranges of the restitution parameter, the cardiac interval, and the stimulation parameters that allow for mapping of stimulation parameters to the restitution parameter for each specified range of the cardiac interval. At 2108, the neurostimulation is adjusted using the stored set of values and/or value ranges of the restitution parameter, the cardiac interval, and the stimulation parameters. In various embodiments, delivery of the neurostimulation is stalled, stopped, or maintained, and/or one or more of the stimulation parameters are adjusted, at 2108. Examples of the stimulation parameters being adjusted include pulse amplitude, pulse width, pulse frequency or inter-pulse interval, duty cycle, waveform (e.g., monophasic or biphasic), polarity, ramping (rate of increase or decrease in the amplitude), and stimulation duration (e.g., daily dose or periodic dose specified as duration of therapy session).

The process of measurement, storage, and adjustment, including steps 2102, 2104, 2106, and 2108, repeats while the patient is being treated with the neurostimulation. At 2110, if it is time for subsequent measurement according to a specified schedule or in response to a specified type event, steps 2102, 2104, 2106, and 2108 are repeated.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A neurostimulation system for stimulating a nerve of a patient's autonomic nervous system using an electrode placed on the nerve, comprising:
    a stimulation output circuit configured to deliver neurostimulation through the electrode;
    a sensing input configured to receive one or more cardiac signals; and
    a control circuit coupled to the stimulation output circuit and the sensing circuit, the control circuit including:

a measurement circuit configured to measure a cardiac interval and a restitution parameter using the one or more cardiac signals;

a restitution analyzer configured to analyze restitution of the restitution parameter, the restitution analyzer including a slope computer configured to compute a restitution slope using values of the restitution parameter measured at a plurality of cardiac intervals, the restitution slope being a rate of change of the restitution parameter with respect to change in the cardiac interval; and a stimulation controller configured to control an autonomic modulation therapy including the delivery of the neurostimulation using the restitution slope, the stimulation controller including:

a comparator configured to compare the restitution slope to a specified target range; and a stimulation adjuster configured to adjust the delivery of the neurostimulation using an outcome of the comparison, the stimulation adjuster configured to stop the delivery of the neurostimulation in response to the computed restitution slope being within the specified target range.

2. The system of claim 1, wherein the measurement circuit comprises an action potential duration (APD) measurement circuit configured to measure an APD parameter as the restitution parameter using the one or more cardiac signals, the APD parameter representative of APD.

3. The system of claim 1, wherein the measurement circuit comprises a conduction velocity (CV) measurement circuit configured to measure a CV parameter as the restitution parameter using the one or more cardiac signals, the CV parameter representative of CV.

4. The system of claim 1, wherein the measurement circuit comprises a QT measurement circuit configured to measure a QT interval as the restitution parameter using the one or more cardiac signals, the QT interval being a time interval between the Q-wave and the subsequent T-wave in a cardiac cycle.

5. The system of claim 1, wherein the measurement circuit comprises T-wave morphology (TM) measurement circuit configured to measure a TM parameter as the restitution parameter using the one or more cardiac signals, the TM morphology parameter representative of an amplitude or time interval associated with a T-wave.

6. The system of claim 1, wherein the stimulation adjuster is configured to adjust one or more parameters of the plurality of parameters in response to the computed restitution slope being outside the specified target range.

7. The system of claim 1, wherein the stimulation adjuster is configured to start the delivery of the neurostimulation in response to the computed restitution slope being outside the specified target range.

8. The system of claim 1, wherein the control circuit comprises an analysis initiator configured to initiate a computation of the restitution slope by the restitution analyzer according to a specified schedule.

9. The system of claim 8, wherein the analysis initiator is configured to initiate the computation of the restitution slope by the restitution analyzer at a period of approximately 21 hours.

10. The system of claim 8, wherein the analysis initiator is configured to initiate the computation of the restitution slope by the restitution analyzer at a specified time each day.

11. The system of claim 1, wherein the control circuit comprises an analysis initiator configured to detect a specified type triggering event and initiate a computation of the restitution slope by the restitution analyzer in response to a detection of the specified type triggering event.

12. The system of claim 1, wherein the measurement circuit is configured to measure a further restitution parameter using the one or more cardiac signals, the restitution analyzer is configured to compute multiple restitution slopes each being the rate of change of one of the restitution parameter and the further restitution parameter with respect to the change in the cardiac interval, and the control circuit is configured to control the delivery of the neurostimulation using the multiple restitution slopes.

13. A method for controlling delivery of neurostimulation to a nerve of a patient's autonomic nervous system through an electrode placed on the nerve, comprising:

sensing one or more cardiac signals;

measuring a restitution parameter using the sensed one or more cardiac signals at a plurality of cardiac intervals covering a specified range of cardiac intervals;

computing a restitution slope using values of the restitution parameter measured at the plurality of cardiac intervals, the restitution slope being a rate of change of the restitution parameter with respect to change in the cardiac interval; and controlling an autonomic modulation therapy including the delivery of the neurostimulation to the nerve using the restitution slope, including:

comparing the restitution slope to a specified target range; and adjusting the delivery of the neurostimulation using an outcome of the comparison, including stopping the delivery of the neurostimulation in response to the computed restitution slope being within the target range.

14. The method of claim 13, comprising introducing the plurality of cardiac intervals by delivering cardiac pacing pulses.

15. The method of claim 13, wherein measuring the restitution parameter comprises measuring an action potential duration (APD) parameter representative of APD, conduction velocity (CV) parameter representative of CV, a QT interval, or a T-wave morphology (TM) parameter representative of an amplitude or time interval associated with a T-wave using the one or more cardiac signals.

16. The method of claim 15, wherein the sensing the one or more cardiac signals comprises sensing an intracardiac electrogram, and measuring the restitution parameter comprises measuring an activation-recovery interval (ARI) as the APD parameter using the intracardiac electrogram, the ARI being a time interval between a first point associated with a maximum negative amplitude change (down slope) in an R-wave and a second point associated with a maximum positive amplitude change (up slope) in a T-wave in the intracardiac electrogram.

17. The method of claim 15, wherein sensing the one or more cardiac signals comprises sensing first and second intracardiac electrograms, and measuring the restitution parameter comprises measuring the CV parameter being a time interval between occurrence of a cardiac event in the first intracardiac electrogram and occurrence of the cardiac event in the second intracardiac electrogram.

18. The method of claim 15, wherein measuring the restitution parameter comprises measuring the CV parameter being a QRS width using the one or more cardiac signals.

19. The method of claim 15, wherein sensing the one or more cardiac signals comprises sensing a subcutaneous electrocardiogram (ECG), and measuring the restitution parameter comprises measuring the QT interval using the subcutaneous ECG.

20. The method of claim 15, wherein measuring the restitution parameter comprises measuring the TM parameter being an amplitude of the T-wave.

21. The method of claim 15, wherein measuring the restitution parameter comprises measuring the TM parameter being a width of the T-wave.

22. The method of claim 15, wherein measuring the restitution parameter comprises measuring the TM parameter being a time interval between a peak and an end of the T-wave.

23. The method of claim 13, comprising initiating a computation of the restitution slope according to a specified schedule.

24. The method of claim 13, comprising:
   detecting a specified type triggering event; and
   initiating a computation of the restitution slope in response to a detection of the specified type triggering event.

25. The method of claim 13, comprising:
   measuring a further restitution parameter using the sensed one or more cardiac signals at the plurality of cardiac intervals covering the specified range of cardiac intervals;
   computing a further restitution slope using the values of the further restitution parameter measured at the plurality of cardiac intervals, the further restitution slope being a rate of change of the further restitution parameter with respect to the change in the cardiac interval; and
   controlling the delivery of the neurostimulation using the restitution slope and the further restitution slope.

* * * * *